(12) United States Patent
Honegger et al.

(10) Patent No.: US 12,011,531 B2
(45) Date of Patent: Jun. 18, 2024

(54) MOTOR-DRIVEN MEDICAL SUCTION PUMP AND METHOD FOR CONNECTING SUCH A SUCTION PUMP TO A POWER SOURCE

(71) Applicant: MEDELA HOLDING AG, Baar (CH)

(72) Inventors: Adrian Honegger, Lucerne (CH); Charles Giezendanner, Morschach (CH)

(73) Assignee: MEDELA HOLDING AG, Baar (CH)

( * ) Notice: Subject to any disclaimer, the term of this patent is extended or adjusted under 35 U.S.C. 154(b) by 293 days.

(21) Appl. No.: 17/605,501

(22) PCT Filed: Mar. 12, 2020

(86) PCT No.: PCT/EP2020/056704
§ 371 (c)(1),
(2) Date: Oct. 21, 2021

(87) PCT Pub. No.: WO2020/216525
PCT Pub. Date: Oct. 29, 2020

(65) Prior Publication Data
US 2022/0203012 A1    Jun. 30, 2022

(30) Foreign Application Priority Data
Apr. 25, 2019 (EP) .................................... 19171192

(51) Int. Cl.
*G08B 23/00* (2006.01)
*A61M 1/00* (2006.01)
(Continued)

(52) U.S. Cl.
CPC ................ *A61M 1/73* (2021.05); *A61M 1/74* (2021.05); *A61M 1/80* (2021.05); *H01R 13/22* (2013.01);
(Continued)

(58) Field of Classification Search
CPC ............ A61M 1/73; A61M 1/74; A61M 1/80; A61M 1/06; A61M 2205/14;
(Continued)

(56) References Cited

U.S. PATENT DOCUMENTS 5,292,232 A      3/1994   Krohn et al.
7,351,066 B2 *   4/2008   DiFonzo ............ H01R 13/6205
                                                    439/39
(Continued)

FOREIGN PATENT DOCUMENTS

DE    4221286 A1    1/1993
EP    0447551 B1    5/1995
(Continued)

OTHER PUBLICATIONS

International Search Report for International Application No. PCT/EP2012/050108, dated Sep. 17, 2012.
(Continued)

*Primary Examiner* — Toan N Pham
(74) *Attorney, Agent, or Firm* — MARSHALL, GERSTEIN & BORUN LLP

(57) ABSTRACT

The present invention relates to a motor-driven suction pump and a method for connecting such a pump. The suction pump has a pump unit for generating a negative pressure which is accommodated in a housing. Further, a terminal box is provided which can be connected to a power source via a connecting cable and has contact elements for supplying the pump unit with a power current. The contact elements are electrically conductively connected to the contact counter elements provided on the housing side and leading to the pump unit when the terminal box is coupled to the housing. In order to increase electrical safety, a sensor, an evaluation unit, and a switch are provided. The sensor is configured to check the coupling of the terminal box. The (Continued)

switch switches a power supply to at least one of the contact elements. The evaluation unit is data-based connected to the sensor and the switch such that the switch connects the contact element to the power current supply when a signal of the sensor confirming the coupling is present and disconnects the power current supply when a signal of the sensor confirming the coupling is absent. In the method according to the invention, at least one contact element which is switched off is first electrically connected to the counter contact element on the housing side, which is provided for supplying current to the pump unit. The power current is then applied to the contact element on the basis of a signal confirming the corresponding contacting.

16 Claims, 4 Drawing Sheets

(51) Int. Cl.
*H01R 13/22* (2006.01)
*H01R 13/62* (2006.01)
*H01R 13/703* (2006.01)
*A61M 1/06* (2006.01)

(52) U.S. Cl.
CPC ..... *H01R 13/6205* (2013.01); *H01R 13/7038* (2013.01); *A61M 1/06* (2013.01); *A61M 2205/14* (2013.01); *A61M 2205/82* (2013.01)

(58) Field of Classification Search
CPC ............... A61M 2205/82; H01R 13/22; H01R 13/6205; H01R 13/7038
See application file for complete search history.

(56) References Cited

U.S. PATENT DOCUMENTS

| | | | | |
|---|---|---|---|---|
| 9,478,901 | B2 * | 10/2016 | Chen | H01R 13/22 |
| 9,647,385 | B2 * | 5/2017 | Suh | H01R 13/6205 |
| 9,735,500 | B2 * | 8/2017 | Magana | H01R 13/64 |
| 2003/0046439 | A1 | 3/2003 | Manke et al. | |
| 2010/0233889 | A1 | 9/2010 | Kiani et al. | |
| 2018/0200423 | A1 | 7/2018 | Agarwal et al. | |

FOREIGN PATENT DOCUMENTS

| | | | |
|---|---|---|---|
| JP | H05-031150 U | 4/1993 | |
| JP | 2005-256421 A | 9/2005 | |
| JP | 2019-017163 A | 1/2019 | |
| WO | WO-2013/102495 A1 | 7/2013 | |
| WO | WO-2015/069095 A1 | 5/2015 | |
| WO | WO-2017194383 A1 * | 11/2017 | A61M 1/06 |

OTHER PUBLICATIONS

European Search Report for Application No. EP19171192, dated Oct. 22, 2021.
Notice of Reason for Refusal for Japanese Patent Application No. 2021-562952, dated Feb. 24, 2023.
Japanese Office Action for Application No. 2021-562952, dated Sep. 20, 2023.

* cited by examiner

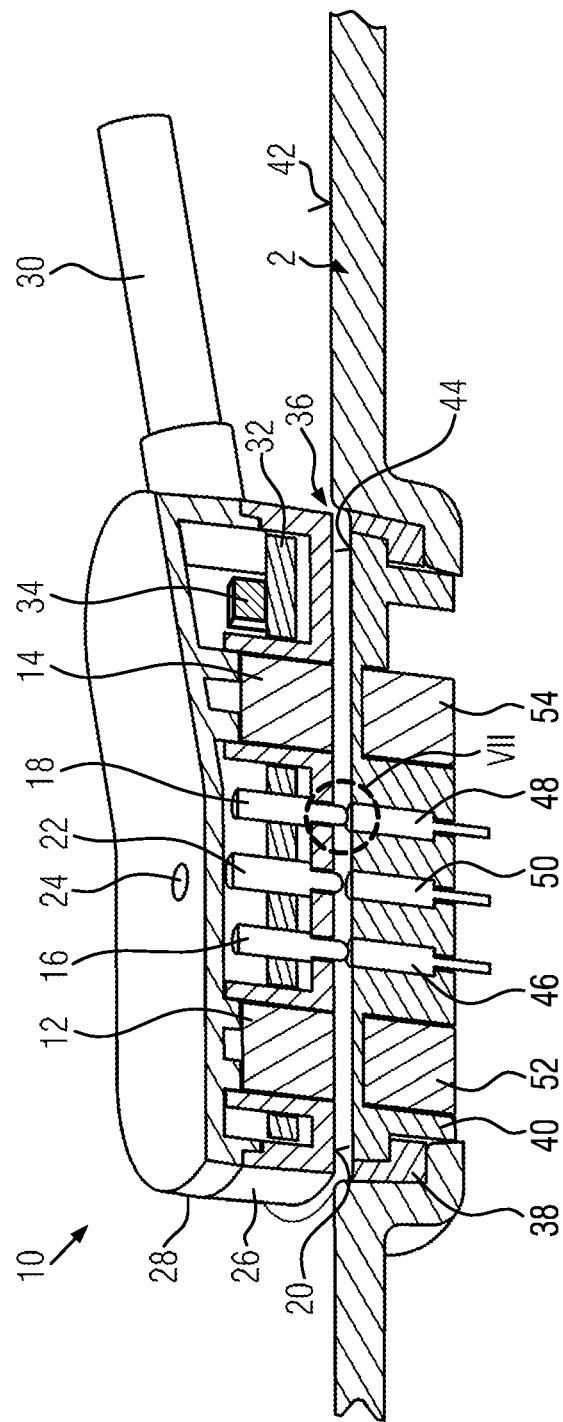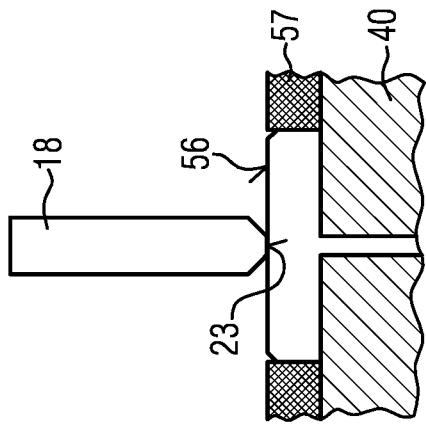

MOTOR-DRIVEN MEDICAL SUCTION PUMP AND METHOD FOR CONNECTING SUCH A SUCTION PUMP TO A POWER SOURCE

CROSS-REFERENCE TO RELATED APPLICATION

This present application is the US national phase of International Patent Application No. PCT/EP2020/056704, filed Mar. 12, 2020, which claims priority to European Application No. 19171192.8, filed Apr. 25, 2019. The priority application, EP 19171192.8, is hereby incorporated by reference in its entirety.

FIELD OF THE DISCLOSURE

The present invention relates to a motor-driven medical suction pump with a pump unit for generating a negative pressure which is accommodated in a housing and with a terminal box which can be mechanically coupled to said housing and which can be connected to a power source via a connecting cable. The terminal box has contact elements to supply the pump unit with a power current. When the terminal box is coupled to the housing, these contact elements are electrically conductively connected to contact counter elements provided on the housing side, which lead to the pump unit.

BACKGROUND

Such a motor-driven pump is known, for example, as an exudate pump. Another configuration of a corresponding suction pump is a breast pump for sucking human breast milk from the female breast. The electrical connection to a power source occurs via a plug-contacting cable, which has a terminal box. The contact elements in this terminal box are usually installed in such a way that they are not exposed on the outside. The contact elements are usually provided as female plug contact elements, whereby the housing has male plug contact counter elements assigned to them, which must first be inserted to some extent into a cavity in the terminal box for plug contacting until an electrical contact is established between the contact elements and the contact counter elements.

The above described generally known arrangement of the contact elements in the terminal box is particularly useful for electrical safety. This prevents the voltage applied to the terminal box from being transmitted unintentionally during normal handling of the terminal box. However, the present invention considers it necessary to improve electrical safety in this respect.

SUMMARY OF THE INVENTION

The invention of the motor-driven medical suction pump provides a sensor, an evaluation unit and a switch. The sensor is configured to check the coupling of the terminal box. The sensor can be a contactless or a touching sensor. The sensor is configured such that it detects the coupling, i.e. the correct coupling of the terminal box to the housing. The correct coupling is defined as the coupling of the terminal box to the housing in which the contact elements are electrically connected to the associated contact counter elements. Thus, for the detection of the correct coupling, it is not sufficient to connect the terminal box to the housing in any way. Instead, the terminal box must be positioned exactly opposite the housing so that the electrical contact between the terminal box and the housing is realized. The evaluation unit is connected to the sensor and the switch in relation to the data. The switch controls the power current. For this purpose, the switch is usually located in the terminal box or a connector plug connected to the supply current on the other side of a connecting cable for plug-in contact. By the data-related connection of the evaluation unit with the sensor and the switch, it is then possible to analyze the sensor signal emitted by the sensor and to connect the power current to the contact element or elements attached to the terminal box through the switch.

With the present invention, a solution is proposed in which the energized contact elements of the terminal box are separated from the power current until a mechanical coupling between the terminal box and the housing is detected. This allows the terminal box with the contact elements provided on it to be handled without the risk of electric shock, even if the connection plug or the connecting cable leading to the terminal box, which can be permanently connected to the supply voltage, is energized.

The present invention can be used in many fields in which good electrical safety is important or in which it cannot be excluded that elements, extremities or media come into contact with the contact elements. Thus, the present invention is particularly suitable for connecting an electrical consumer in a damp room or in an area in which vapors or gases, in particular electrically conductive gases or explosive gases, are present. The solution according to the invention is basically suitable for any electrical contact to an electrical consumer which is provided in a housing. The terminal box can be coupled with said housing and exhibits the contact elements for energizing the consumer with the power current, in order to be electrically conductively connected to the contact elements provided on the housing side and leading to the consumer when the terminal box is mounted on the housing. The electrical contact has a sensor, an evaluation unit, and a switch as described above. Insofar as the description of the invention refers to the fact that the power current is supplied to the pump unit in the housing, this does not mean that the power current is not also supplied to other components within the housing. Rather, the housing of the suction pump according to the invention usually also accommodates an electronic control device, which controls or switches the power current, as well as usually an accumulator, via which the electrical energy introduced into the housing can be stored.

As described above, the sensor can be any sensor that detects the mechanical coupling, in particular the correct mechanical coupling of the terminal box to the housing. The sensor can be a magnetic switch, a proximity sensor or an optical sensor. The sensor should at least be provided on the terminal box in order to detect the approach and mechanical coupling of the terminal box to the housing and to communicate directly with the evaluation unit provided on the connection side.

A robust and reliable solution is proposed according to a preferred further development of the present invention, according to which the sensor has a sensor element, to which a sensor counter element is assigned on the housing side, wherein the sensor element emits a signal confirming the coupling depending on the relative position to the sensor counter element. At least one of the contact elements and the sensor element are arranged in the terminal box such that, when the terminal box is mechanically coupled to the housing, the contact element is first electrically connected to the associated contact counter element and only afterwards is the sensor element positioned relative to the sensor counter element such that a signal confirming the coupling is emitted so that the power current is applied. In this preferred further development, the sensor element and sensor counter element are subsequently assigned to each other such that their electrical contacting is preferred to transmit the sensor signal. In its simplest form, a sensor element is an electrical pin that interacts with a contact surface formed by the sensor counter element. In a simple configuration, the sensor element and/or the sensor counter-element is designed as a downstream element which projects in the coupling direction of the terminal box when it is mechanically coupled to the housing from the terminal box or on the housing side, whereas in the same coupling direction it is arranged behind the contact element or contact counter-element. The contact element and/or the contact counter-element will be pre-tensioned by a spring in the coupling direction and held movably in order to permit, after their contacting, the path of the terminal box which still has to be covered to be in the direction of the box until the terminal box is mechanically coupled to the housing and/or the sensor element and the sensor counter-element are electrically connected to one another. The sensor element and sensor counter element can be spring pre-tensioned and movable in an appropriate manner to allow reliable contacting despite given tolerances and inaccuracies in the mechanical coupling of the terminal box and housing.

Any elastic element which can absorb and store a restoring force by deformation can be regarded as a spring in the aforementioned sense. It is only important that the contact element and/or the contact counter element or the sensor element and the sensor counter element in the coupled state engage with each other and/or lie against each other with a certain pretension force.

The contact counter elements are preferably in a fixed and immovable position in the housing or relative to it. The compensating movement is preferably effected solely by moving contact elements on the side of the terminal box.

The present invention is based in particular on the consideration that with the possibility of switching on the power current only after the terminal box has been positioned on the housing, new possibilities of contacting are given. Because with the solution according to the invention, it is not necessary to mechanically protect the normally energized contact elements from contact. For example, with the present invention it is possible to configure the terminal box and/or the housing at least in the contact area with a contact surface that is free of set-off and against which the other of the terminal box and housing is applied in the coupled state. According to this, the contact surface is the surface over which the terminal box and the housing come into contact in the coupled state. The contact elements are usually located within this contact surface. In any case, the further development offers the possibility of configuring the terminal box and/or the housing such that no flashes or other edges or undercuts occur in the area of the transmission of the power current into the housing, where contamination could settle. The further development thus makes it possible to configure the housing or the terminal box such that it is easy to clean and/or disinfect. The development is particularly suitable for the transmission of the power current to a housing in the medical field.

The further development discussed above also dispenses with mechanical form-fit elements with which the terminal box and the housing are mechanically connected and coupled. In order to compensate for this, the present invention proposes contact-free holding means which hold the terminal box in the coupled state to the housing. Preferably, the terminal box is held to the housing by magnetic force. Permanent magnets, a magnetizable material and/or electromagnets can be used for this purpose. Suitable are all solutions known, for example, from the prior art EP 2 287 972 B1, CN 207 853 072 U or CN 202 050 089 U for the mechanical coupling of terminal box and housing for the transmission of a power current.

The solution according to the invention is not limited to a certain voltage of the power current. However, particular consideration will be given to configurations to connect consumers to the usual power sources in a building, such as a hospital, retirement home or residential building. The electrical contact of the present invention is usually transmitted at a voltage of not more than 230 volts. The power voltage transmitted between the contact elements and the contact counter elements can also be transformed to low voltage. In particular, medical suction pumps are usually equipped with a 12 volt power unit to allow the suction pump to be powered by an autonomous energy source, a battery or a rechargeable accumulator, usually built into the housing. In such low-voltage solutions, as well, the configuration of the electrical contact according to the invention proves to be advantageous, since especially in the medical field, even the slightest current impulses to patients or infants can be avoided. Thus, the electrical contacting according to the invention is particularly suitable for any connection from a consumer in an electrically operated medical device to an external power current fed via a connecting cable.

In the further development of the mechanical coupling via a magnetic force to be discussed here, an exact positioning of the coupled terminal box can be achieved by a single magnetic element which, together with a single magnetic counter element on the housing side, holds the terminal box in a predetermined orientation on the housing. For this purpose, the magnetic element or the magnetic counter-element should have an asymmetrical shape and/or asymmetrical arrangement relative to an axis of symmetry of a trough which accommodates the terminal box and, if appropriate, surrounds it at the end with some play, wherein the base area of the terminal box and the base area of the trough should at least approximately correspond to one another. The trough and/or the terminal box itself can also have a specific contour that specifies a predetermined orientation of the terminal box in the trough.

Preferably, at least two magnetic elements are provided on the terminal box, which are provided with different poles and are effective in the coupled state for clear positioning of the terminal box relative to the housing. The at least two magnetic elements subsequently ensure that the terminal box in the mechanically coupled state lies in the correct manner, unambiguously defined by the at least two magnetic elements, against the contact surface on the housing side. If the magnetic elements with different poles are applied in the wrong orientation to the contact surface usually provided on the housing side in a trough, repulsive magnetic forces result due to the housing side magnets, so that a mechanical coupling is not possible. Thereafter, the at least two magnetic elements of different polarity allow an unambiguous assignment of the position of the terminal box on the housing in the coupled state, with the result that the contact elements are electrically connected to the contact counter elements in the correct alignment and arrangement.

According to a preferred further development of the present invention, a counter-housing is proposed which is connected to the housing and has a contact surface which is provided at least approximately flush with an outer surface of the housing. The counter housing usually accommodates the contact counter elements and holds the connecting cables or other electrical conductors provided to the contact counter elements on the housing side for the transmission of the power current to at least one consumer in the housing. The main function of the counter housing is usually to immovably hold the contact counter elements and to make their contact surface available on the outside as well as to be connected to the actual housing. Accordingly, the terminal box is a component of a contact pair consisting of the terminal box on the one hand and the counter housing on the other hand. The terminal box is usually connected to the connecting cable, while the cabling inside the housing to the consumer, in particular the pump unit, goes out from the counter box. It goes without saying that these electrical conductors do not necessarily have to be electrically connected directly to the pump unit. In many cases, contacting is usually carried out with the interposition of a controller which receives control commands and can make the transmission of the power current to the consumer dependent on various influencing variables.

The housing usually has an opening in which the counter housing is inserted. For medical applications in particular, the counter housing is flush or approximately flush with the outer surface of the housing, for example in a trough formed by the housing. This configuration of the components of the electrical contact on the housing side also makes it possible to create a configuration that is easy to clean or sterilize.

The terminal housing and/or the counter housing are usually made of an electrically insulating material such as ceramic or plastic. The contact elements or contact counter elements can be easily attached and held to the corresponding housing. In particular in the case of mechanical coupling by means of magnetic force, however, it is preferable to form the contact surface on the housing side by means of an electrically non-conductive coating which is provided on the outside at least approximately flush or flush with the contact surfaces of the contact counter elements. This coating is usually a coating made of a damping plastic, preferably silicone or TPE. The coating can be applied to the counter housing, e.g. glued or injection molded. The outer surface of the coating and the contact surface of the contact counter elements, via which these are electrically contacted with the contact elements, are approximated, preferably completely flush, so that on the housing side a flat and smooth surface results, which is formed partly by the coating and partly by the contact surfaces, and which is easy to clean. It goes without saying that the contact counter elements are usually sealed and passed through the coating. The connection can be the result of a composite injection molding in which the terminal box made of a hard plastic together with the contact counter elements embedded in it by overmolding, which initially protrude over the surface of the terminal box, is overmolded with a plastic forming the coating. The coating can also be applied subsequently, wherein the recesses for receiving the free end sections of the contact elements can have smaller dimensions than the contact elements so that these are pressed into the coating, resulting in the desired sealing. The coating can also be bonded to the contact counter elements.

With regard to tolerance compensation, it is proposed according to the present invention to provide the contact surface formed by the contact element smaller in area than the contact counter surface of the contact element intended for contact with the contact element. While the contact element is usually intended as a pin, the contact counter surface is many times larger than the end face of the contact pin so that certain tolerances within the correct positioning of the terminal box relative to the housing are possible without affecting the desired transmission of the power current. In particular, this solution compensates for the absence of form-fit elements that align the terminal box with the housing in a predetermined manner, while they should be avoided with regard to the desired smooth surface in the contact area. It goes without saying that the size of the contact counter surface must be selected such that, with conceivable tolerances, the contact element assigned to each contact counter surface is always electrically conductively contacted with the corresponding contact counter surface when the terminal box and housing are mechanically coupled. The tolerance and the play allow a movement between the contact surface and the contact counter surface, which favors a self-cleaning of the surfaces causing the electrical contact. Due to the relative movement, contamination or metallic oxides on the surfaces are scraped off so that a good electrical contact is permanently guaranteed.

In order to check the correct contacting for the transmission of the power current, the solution according to the invention preferably has an optical indicator which indicates the status of the power current supply. This optical indicator is usually a control lamp which can be provided on the housing and/or terminal box. In the simplest case, the optical indicator is provided as an LED on the terminal box and data-based connected to the evaluation unit so that the LED is switched on at the same time when the switch is released to transmit the power current.

According to a preferred further development of the present invention, the contact elements or the contact counter elements are arranged with different polarity and the magnetic elements are offset to a central longitudinal axis which is usually formed and predetermined by the terminal box, if necessary, also by the counter housing. Such an asymmetrical design increases the electrical safety, since due to the magnets, an unambiguous positioning of the terminal box on the housing is predetermined and the contact elements or contact counter elements do not lie on the central longitudinal axis so that during mechanical coupling, the contact element is also necessarily contacted with the correct contact counter element.

Based on corresponding considerations, it is proposed, according to a preferred further development of the present invention, that for each polarity at least two contact elements or contact counter elements are provided which define corner points of a base surface in a top view of the contact surface, wherein the sensor element or the sensor counter element within this base surface is preferably arranged asymmetrically to this base surface and especially preferably at an edge of the base surface. This configuration also prevents incorrect connection of the contact elements with the contact counter elements. In addition, the number of contact elements or contact counter elements provided per polarity increases the safety when transmitting the power current. The base surface is preferably a rectangular surface, wherein the contact elements or contact counter elements of the same polarity usually lie on a straight line which forms a side face of the rectangle. The contact elements or contact counter-elements of the other polarity are opposite thereto, wherein the parallel rows of contact elements are usually separated from one another by the longer side faces of the rectangle. With such a configuration, not all contact elements or contact counter elements lie on the same line. Rather, as described above, the contact elements or the contact counter elements are opposite each other and arranged on the same lines. The sensor element or the sensor counter element usually lies on one of these edges. All contact elements are preferably located between the magnetic elements, which further reduces the risk of incorrect electrical contacting. This arrangement also prevents external magnetic plugs or other charging plugs from being connected to the device. An electrical overvoltage with consequential damage can thus be prevented.

According to a preferred further development of the present invention, a contact element or a contact counter element can be integrated into the magnetic element. The contact element thereby can be surrounded by a ring-shaped magnetic element or be formed by a metallic surface of the magnet itself. The configuration can be realized on the terminal box and/or on the housing side. The magnetic element can also be formed by the contact element itself, in particular if it is an electromagnetic element which becomes magnetic by energization.

According to its parallel aspect, the present invention proposes a method for connecting a consumer, for example, a motor-driven medical suction pump with a pump unit for generating a negative pressure, to a power source for the power current. In the method according to the invention, at least one of the contact elements for energizing the consumer is first electrically connected to the contact counter element on the housing side. The housing side is the side of the contact that is assigned to the consumer, especially the motor-driven suction pump. The connection occurs when the contact element is de-energized. After a signal has been emitted on the basis of a sensor confirming the contacting, in the method according to the invention, the power current is applied to the contact element. The method is preferably performed simultaneously for all contact elements of the contacting between the consumer and the terminal box so that the power current is applied to all energized contact elements at the same time. The sensor confirming the contacting can be a sensor directly detecting the electrical contacting between the contact element and the contact counter element. In other words, the sensor detects the electrical contact of the contact element and contact counter element. Alternatively, the sensor can indirectly be connected to the contact by detecting the correct positioning of the terminal box relative to the housing of the consumer.

BRIEF DESCRIPTION OF THE SEVERAL VIEWS OF THE DRAWING

Further details and advantages of the present invention result from the following description of embodiments in conjunction with the drawing. Therein:

FIG. 6 shows a perspective, partially sectional side view of the terminal box according to FIGS. 3 to 5 when coupled to the suction pump housing; and FIG. 7 shows a magnified detail VII according to FIG. 6.

DETAILED DESCRIPTION OF THE PREFERRED EMBODIMENTS

Figure 1:
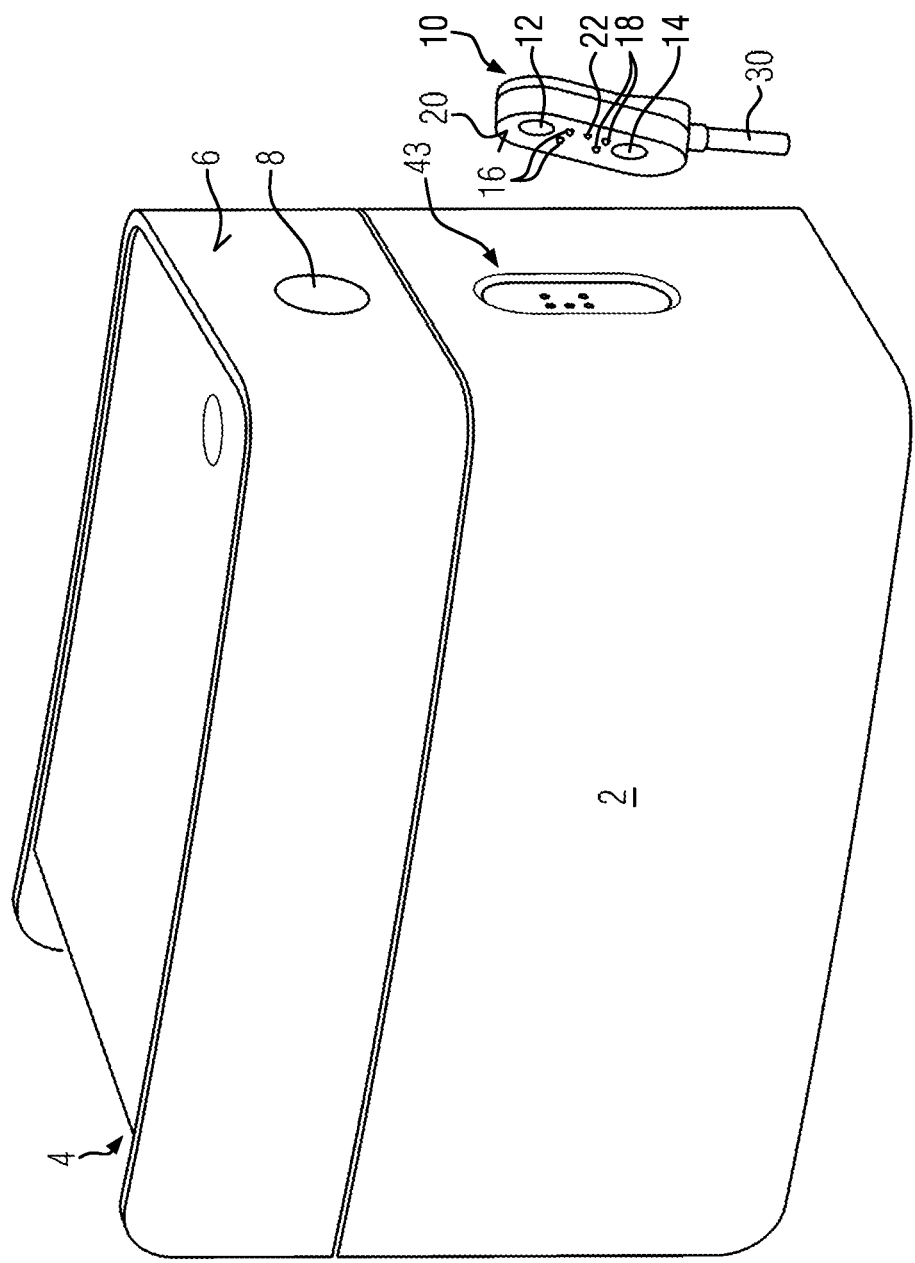
FIG. 1 shows a perspective side view of a medical suction pump for sucking off exudate before electrical contacting.
Figure 2:
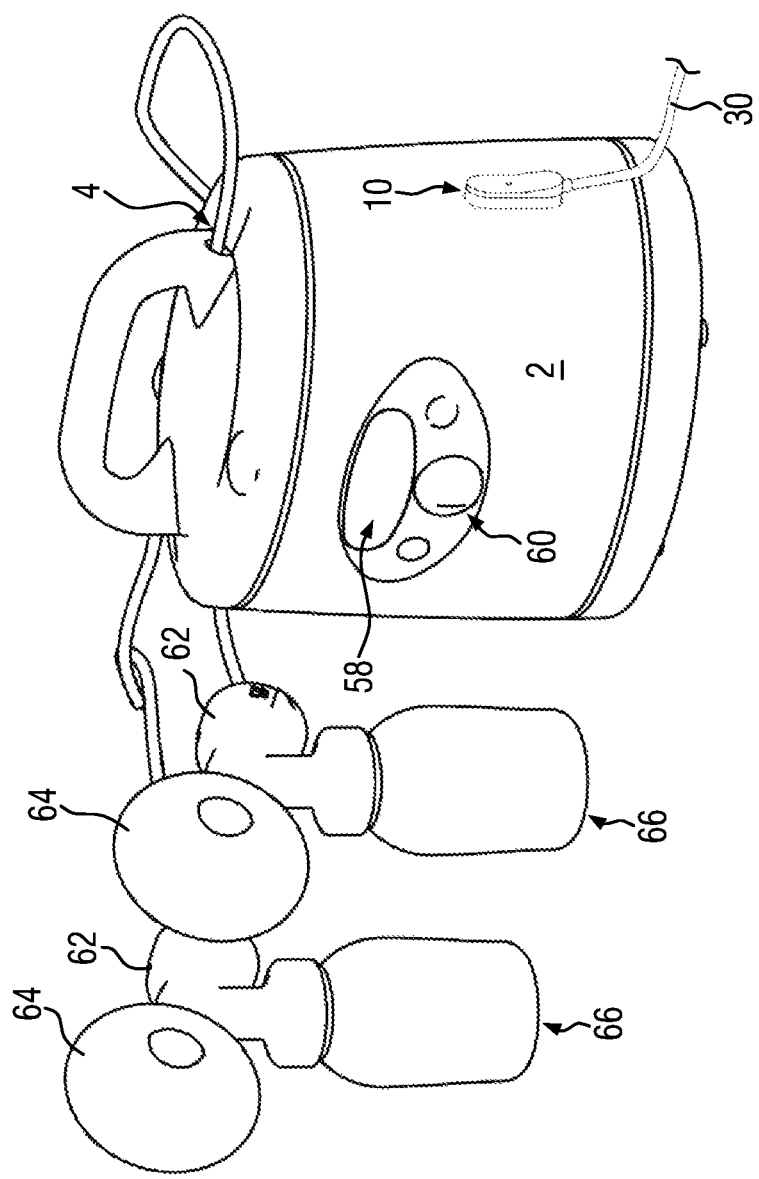
FIG. 2 shows a perspective side view of a medical suction pump with breast pumps for sucking human breast milk after contacting.

FIGS. 1 and 2 each show examples of medical suction pumps on the basis of an exudate pump (FIG. 1) or a suction pump for pumping human breast milk from the female breast (FIG. 2). The examples on both sides show in their housing 2 each a pump unit which is not shown in the drawing, by means of which a negative pressure is generated which, for example, is present at an interface 4 to which, for example, a negative pressure hose can be connected. This interface 4 is illustrated in FIG. 2. In the execution example embodiment shown in FIG. 1, the interface 4 is located on a rear side, the details of which are not visible. The interface 4 communicates here with an exudate container which can be mechanically coupled to the housing 2 and which is configured as a disposable part adapted for collecting exudate. The rear side is provided parallel and opposite to a front side specified with reference sign 6 which is configured for contacting with the power current and is provided with a power switch 8.

Figure 3:
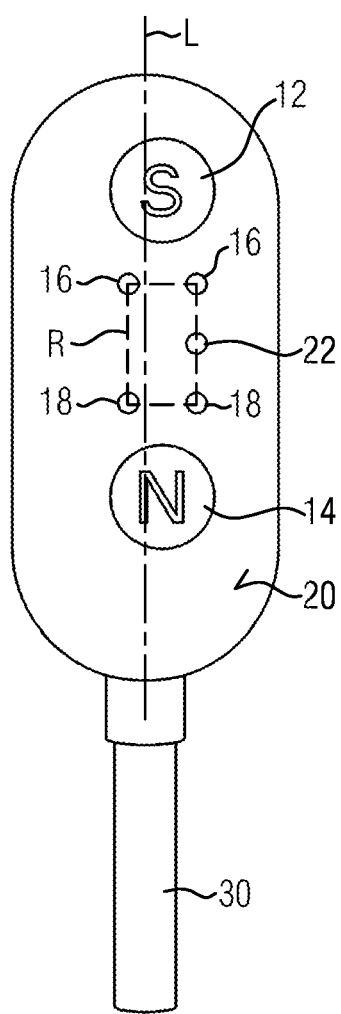
FIG. 3 shows a top view of the contact surface of an embodiment of a terminal box.
Figure 4:
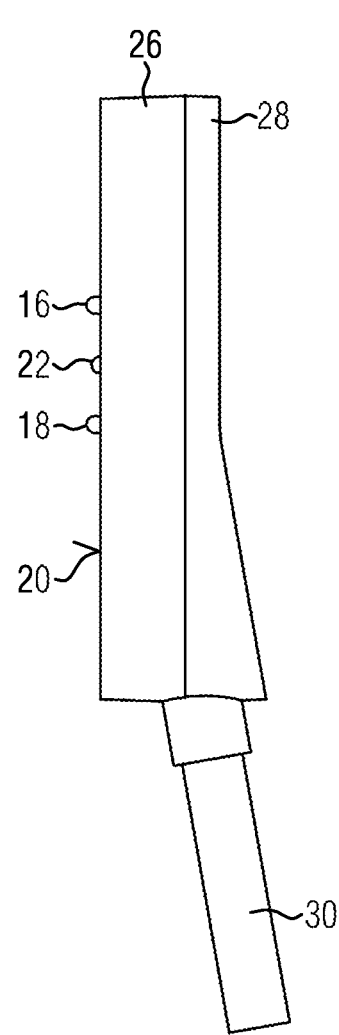
FIG. 4 shows a side view of the terminal box according to FIG. 3.

The contact with the power current occurs in both embodiments via a terminal box 10 which is provided with two magnetic elements 12, 14, each assigned to different poles S, N, and accommodating several contact elements 16, 18 between them which project above a contact surface 20. The contact elements 16 are assigned to one polarity of the power current, the contact elements 18 to the other polarity. As illustrated in FIG. 3, the contact elements 16, 18 tension a rectangular surface R. On the right edge in FIG. 3 of this rectangle lies a sensor element 22 which is presently configured as a sensor pin. Thus, the contact elements 16, 18 and the sensor pin 22 are exposed in the contact surface 22. In fact, the contact elements 16, 18 and the sensor pin 22 project beyond the contact surface 20. As shown in FIG. 4, the contact elements 16, 18 with their free contact surfaces 23 project further away from the contact surface 20 than the sensor pin 22.

Figure 5:
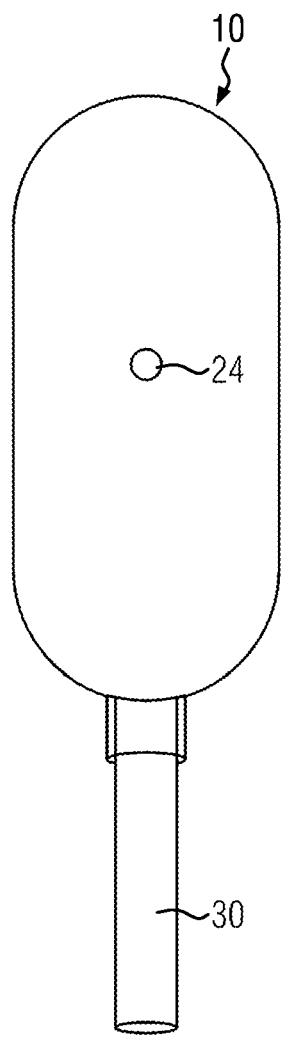
FIG. 5 shows a rear top view of the terminal box according to FIGS. 3 and 4.

The rear side of the terminal box 10 is illustrated in FIG. 5. There, an LED 24 is exposed as an optical indicator. The terminal box 10 is configured in two parts, wherein a connecting cable 30 is led into the terminal box 10 between a lower part 26 and an upper part 28. The connecting cable 30 has at its other end a plug for plug contacting in a conventional socket for 230/110 V connection and can be provided there with an electrical ballast which transforms the voltage to 12 V and feeds the power current into the terminal box 10 with this voltage.

As in particular shown in the synopsis of FIGS. 3 and 4, the contact surface 20 of the terminal box 10 is completely flat. The magnetic elements 12, 14 are embedded into the contact surface 20 without any offset. In other respects as well, the terminal box 10 is configured without undercuts and smoothly. It has a rectangular base with rounded corners. The configuration of the terminal box 10 avoids edges or undercuts in which dirt and bacteria can settle. A connecting piece leading the connecting cable 30 and intended as part of the terminal box 10 can also pass conically or with a radius into the actual terminal box 10 in order to meet the requirement mentioned above as best as possible.

The partially sectioned illustration of the terminal box 10 according to FIG. 6 schematically illustrates some of the components provided in the terminal box 10. A circuit board 32 is electrically conductive connected to the contact elements 16, 18 and the sensor pin 22. The circuit board 32 holds a switch 34, which is data-based connected to an evaluation unit formed by the equipped circuit board 32 itself.

FIG. 6 illustrates the approach of the terminal box 10 to the box 2 in the framework of contacting. The housing 2 has a recess 36 in which a counter housing 40 is inserted by means of an interposed elastomeric seal 38. The surface of the seal 38 and the surface of the counter housing 40 lie slightly within an outer surface 42 of the housing and form a contact surface identified by reference sign 44 on the housing side in a trough 43 offset inwards by less than 3 mm, the dimensions and shape of which correspond approximately to the dimensions and shape of the contact surface 20 of the terminal box 10. It goes without saying that the trough 43 is slightly larger than the contact surface 20.

In the contact surface 44 contact counter elements 46, 48 which are provided for contacting with the contact elements 16, 20 are exposed. A sensor counter pin identified with reference sign 50 is provided as the sensor counter element. Corresponding to the magnetic elements 12, 14, magnetic elements 52, 54 which respectively attract magnetic counter elements 12 and 14 are received within the counter housing 40 and held by it.

Due to the force of the magnets 12, 52 or 14, 54 on both sides, the terminal box 10 is pulled in the direction of the counter housing 40 when approaching the housing 2. The magnetic force causes the terminal box 10 to be precisely positioned relative to the housing 2 so that the contact elements 16, 18 and the sensor pin 20 which are formed within the contact surface 44 by the contact elements 46, 48 and the sensor pin 50 respectively are flush with the contact counter surface 56.

An example of a contact counter surface 56 is illustrated in FIG. 7. The contact pin 18 forming the contact element tapers at its free end and forms a contact surface 23 which is smaller compared to the cross-section of the contact pin 18, nevertheless essentially circular. The contact counter surface 56 formed by the contact counter element 48 is considerably larger so that an electrical contact between the contact elements 16, 18 and the associated contact counter elements 46, 48 is reliably ensured even with a relative offset of the terminal box 10 relative to the ideal position.

As shown in FIGS. 4 and 6, the free end of the sensor pin 22 is located closer to the contact surface 20 than the assigned contact surfaces 23 of the contact elements 16, 18. These contact surfaces lie in a plane parallel to the plane of the contact surface 20. The free end of the sensor pin 22 lies between said plane and the contact surface 20. Thus, when the terminal box 10 approaches the housing 2, the sensor pin 22 projects less far from the contact surface 20 in the coupling direction than the contact elements 16, 18. Accordingly, the sensor pin 22 is a downstream contact pin which first hits the contact counter surface of the associated sensor counter pin 50 after all contact elements 16, 18 have usually been contacted with the associated contact counter elements 46, 48 beforehand. The contact counter element 48, for example, can be short-circuited with the sensor counter element 50 on the housing side. For example, by measuring the electrical resistance from the contact element 18 into the contact counter element 48 and from there into the sensor counter element 50 to the sensor element 22, the coupling of the terminal box 10 to the housing 2 can be detected. The circuit provided on circuit board 32 then sends a signal to the switch 34, which releases the power current in order to feed the power current into the housing 2 via the contact elements 16, 18. The LED 24 is switched on at the same time.

The sectional view according to FIG. 6 also illustrates the essentially offset-free configuration on the housing side. The housing 2 merges into the surface of the counter housing 40 via a sealing lip formed by the seal 38, almost uniformly and without any offset. In this respect, too, it is prevented that bacteria or dirt settle at this point of the electrical contact. In addition, the outer surface of the counter housing facing the terminal box 10 can be coated with a flexible coating so that the terminal box 10 which is attracted by the magnetic force does not hit the housing 2 without damping.

In this context, FIG. 7 illustrates an electrically non-conductive coating 57 which is firmly applied to the counter-housing 40 and the surface of which is level and flush with the contact counter surface 56. This coating 57 can be configured in one piece with the seal 38. The coating 57 is preferably at least approximately level with the outer surface 42 surrounding the contact surface 40.

The solution according to the invention with a switch which switches the power current to the contact elements only when these are applied to the contact counter elements and are in contact with them, and accordingly switches off the power current before the contact elements are separated from the contact counter elements, prevents spark formation or an electric arc especially when the contact of the contact elements is separated, resulting in an increase in the lifetime of the electrical contact. The contact surfaces do not burn due to an electric arc between the not yet contacted contact elements. The electrical contacts formed by the contact elements 16, 18 also remain voltage-free so that there is no impairment to health and/or danger from a voltage applied to the contact elements 16, 18. The voltage is only switched on when the contact elements 16, 18 are contacted with the assigned counter elements 46, 48. These are located either flat in the surface of the housing 2 or in a slight depression. In any case, however, in the embodiment shown, the terminal box 10 protrudes beyond the contact elements 16, 18 to a large extent so that after mechanical coupling of the terminal box 10 to the housing 2, the contact elements 16, 18 cannot be touched by a user and/or contacted with electrically conductive media such as liquid or gas. In this respect, the flexible coating on the outer surface of the counter housing 40 can also provide additional sealing and thus improved electrical safety.

When coupling is done, usually after releasing the power current, the LED 24 is also switched on so that the user is informed of the contact.

The magnetic elements 12, 14 and the associated magnetic counter elements 52, 54 provide an unambiguous positioning. In addition, the contact elements 16, 18 tension a rectangle, which is identified by reference sign R in FIG. 3. Over the longer side of the rectangle R, the contact elements 16 of one polarity are relatively far away from the contact elements 18 of the other polarity. In between, the sensor element 22 is located. The rectangle R is located between the magnetic elements 12, 14. As evident, the central longitudinal axis of the rectangle R is eccentric to a central longitudinal axis L of the terminal box 10. Due to the elongated configuration of the terminal box 10 and the contact surface 44 which is slightly offset backwards to accommodate the same on the housing side, the magnetic forces of the magnetic elements 12, 14 result in a unambiguous positioning which cannot be interchanged due to the magnetic forces of the different poles.

The fact that the contact counter surfaces 56 are larger than the contact surfaces 23 formed by the contact elements 16, 18 and the sensor pin 22 promotes reliable contacting. The contact elements 16 of one polarity and the contact elements 18 of the other polarity are evidently located on a line formed by the opposite, narrower side faces of the rectangle R. The contact elements of different polarity accordingly do not lie on the same line. The creepage distance from the contact elements 16 of one polarity to the contact elements 18 of the other polarity given on the contact surface 20 is increased. The space in between is used for the arrangement of the sensor element 22 which lies on an edge of the rectangle R and thus in the present case exactly on a connecting line between one of the contact elements 16 and the other of the contact elements 18.

The embodiment of a motor-driven suction pump illustrated in FIG. 2 comprises the housing 2 which forms the previously described connection possibility for the coupling of the terminal box 10 and is furthermore provided with a display 58 and control elements 60 for the input of operating parameters. Two connecting parts 62 with one breast cap 64 each to one bottle 66 each are connected to the suction side of the motor-driven medical suction pump via the interface 4.

REFERENCE SIGN LIST 2 housing
4 interface
6 front side
8 power switch
10 terminal box
12 magnetic element, south
14 magnetic element, north
16 contact element
18 contact element
20 contact surface
22 sensor element/sensor pin
24 LED
26 lower part
28 upper part
30 connecting cable
32 circuit board
34 switch
36 recess
38 seal
40 counter housing
42 outer surface
43 trough
44 contact surface
46 contact counter element
48 contact counter element
50 sensor counter pin
52 magnetic counter element
54 magnetic counter element
56 contact counter surface
57 coating
58 display
60 control element
62 connecting part
64 breast cap
66 bottle
R rectangle
L central longitudinal axis of the terminal box 10

What is claimed is:

1. A motor-driven medical suction pump with a pump unit for generating a negative pressure which is accommodated in a housing and with a terminal box which can be mechanically coupled to said housing and which can be connected to a power source via a connecting cable and has contact elements to supply the pump unit with a power current which, when the terminal box is coupled to the housing, are electrically conductively connected to contact counter elements provided on the housing side, which lead to the pump unit,
a sensor, an evaluation unit, and a switch are provided, in that the sensor is configured to check the coupling of the terminal box, in that the switch supplies the power current to at least one of the contact elements, and in that the evaluation unit is data-based connected to the sensor and the switch so that the switch connects the contact element to the power current supply when a signal of the sensor confirming the coupling is present and disconnects the power current supply when a signal of the sensor confirming the coupling is absent.

2. The motor-driven medical suction pump according to claim 1, the sensor has a sensor element to which a sensor counter element is assigned on the housing side, in that the sensor element emits a signal confirming the coupling as a function of the relative position with respect to the sensor counter element, wherein at least one of the contact elements and the sensor element are arranged in the terminal box such that, when the terminal box is mechanically coupled to the housing, the contact element is first electrically connected to the associated contact counter element and only subsequently, the sensor element is positioned relative to the sensor counter element such that a signal confirming the coupling is emitted.

3. The motor-driven medical suction pump according to claim 1, the terminal box is held on the housing by means of magnetic force, wherein preferably the terminal box has at least two magnetic elements which are effective with different poles on a contact surface of the terminal box, opposite the housing in the coupled state, for the unambiguous positioning of the terminal box relative to the housing.

4. The motor-driven medical suction pump according to claim 1, the terminal box and/or the housing have a contact surface which is free of offset and against which the respective other of the terminal box and the housing is in contact in the coupled state.

5. The motor-driven medical suction pump according to claim 1, a counter housing (40) which is connected to the housing (2) and has a contact surface (44) contacting the terminal box (10) in the coupled state and which is provided at least approximately flush with an outer surface (42) of the housing (2).

6. The motor-driven medical suction pump according to claim 1, the contact surface on the housing side is formed by an electrically non-conductive coating which is provided on the outside at least approximately flush with contact counter surfaces of the contact counter elements.

7. The motor-driven medical suction pump according to claim 1, a contact surface formed by the contact element is smaller in area than a contact counter surface of the contact counter element provided for contacting the contact element.

8. The motor-driven medical suction pump according to claim 1, an optical indicator (24) for indicating a status of power current supply.

9. The motor-driven medical suction pump according to claim 1, the contact elements or contact counter elements are arranged with different polarity and magnetic elements are arranged offset with respect to a central longitudinal axis (L) of the terminal box or the counter housing.

10. The motor-driven medical suction pump according to claim 1, the contact elements are flexibly supported in the terminal box.

11. The motor-driven medical suction pump according to claim 1, at least two contact elements or contact counter elements are provided for each polarity, which, in a top view of the contact surface, define corner points of a base surface (R), and in that the sensor element or the sensor counter element is arranged within this base surface (R).

12. The motor-driven medical suction pump according to claim 1, all the contact elements or contact counter elements are provided between magnetic elements.

13. The motor-driven medical suction pump according to claim 1, not all contact elements (16; 18) or contact counter elements (46; 48) are arranged in a line.

14. The motor-driven medical suction pump according to claim 1, the contact elements or contact counter elements in the uncoupled state project through the contact surface assigned to them.

15. The motor-driven medical suction pump according to claim 1, at least one contact element or contact counter element is integrated in a magnetic element.

16. A method for connecting a motor-driven medical suction pump with a pump unit for generating a negative pressure, which is accommodated in a housing, to a power source for a power current, in which contact elements which are held in a terminal box and lead to the current source are electrically connected to contact counter elements on the housing side in the case of at least one contact element which is de-energized, in order to supply current to the pump unit, and the power current is subsequently applied to the contact element on the basis of a signal emitted by a sensor confirming the corresponding contacting.

* * * * *